United States Patent
Stoessel et al.

(10) Patent No.: US 7,589,224 B2
(45) Date of Patent: Sep. 15, 2009

(54) METHOD FOR PRODUCING IRIDIUM(III) KETO KETONATES

(75) Inventors: Philipp Stoessel, Frankfurt Am Main (DE); Ingrid Bach, Hofheim (DE); Amir Parham, Frankfurt (DE); Esther Breuning, Niedernhausen (DE); Hubert Spreitzer, Viernheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/659,898

(22) PCT Filed: Aug. 10, 2005

(86) PCT No.: PCT/EP2005/008670

§ 371 (c)(1),
(2), (4) Date: Sep. 20, 2007

(87) PCT Pub. No.: WO2006/018202

PCT Pub. Date: Feb. 23, 2006

(65) Prior Publication Data

US 2008/0132720 A1    Jun. 5, 2008

(30) Foreign Application Priority Data

Aug. 12, 2004   (EP)   .................. 04019137

(51) Int. Cl.
*C07F 15/00*   (2006.01)
(52) U.S. Cl. .................................... 556/136
(58) Field of Classification Search .................. 556/136
See application file for complete search history.

(56) References Cited

U.S. PATENT DOCUMENTS

| 7,084,273 B2 | 8/2006 | Stössel et al. |
| 2006/0142604 A1 | 6/2006 | Bach et al. |

FOREIGN PATENT DOCUMENTS

| EP | 1088812 A2 | 4/2001 |
| WO | WO-02/060910 A1 | 8/2002 |
| WO | WO-2004/085449 A1 | 10/2004 |

OTHER PUBLICATIONS

Collins, et al., "Synthesis, Characterization, and Molecular Structure of Bis(tetraphenylcyclopentadienyl)rhodium(II)," Organometallics, 1995, vol. 14, pp. 1232-1238.
Liu, et al., "Synthesis and Structural Characterization of Novel Organometalic, Rh(III), Bis(acetylacetonate) Complexes," Organometallics, 2004, vol. 23, No. 15, pp. 3584-3586.
Liu, et al., Organometalics, ACS, Washington, D.C., US, 2004, pp. 1-3.
Dwyer, et al., "The Preparation of Tri-acetylacetone-Rhodium-(iii) and -Iridium(III)," J. Amer. Chem. Soc., 1953, vol. 75, pp. 984-985.
Bennett, et al., "Y-Carbon-Bonded 2,4-Pentanedionato Complexes of Trivalent Iridium," Inorganic Chemistry, 1976, vol. 15, No. 11, pp. 2936-2938.

*Primary Examiner*—Porfirio Nazario Gonzalez
(74) *Attorney, Agent, or Firm*—Connolly Bove Lodge & Hutz LLP

(57) ABSTRACT

Process for the preparation of rhodium(III) and iridium(III) ketoketonates. The present invention describes a process for the preparation of rhodium and iridium compounds which are used as starting compound for various organorhodium compounds and organoiridium compounds, in which the reaction, starting from a rhodium(III) or iridium(III) salt, is carried out in at least two steps, where different solvents or solvent mixtures are used in each.

32 Claims, No Drawings

METHOD FOR PRODUCING IRIDIUM(III) KETO KETONATES

RELATED APPLICATIONS

This application is a national stage application (under U.S.C. §371) of PCT/EP2005/008670, filed Aug. 10, 2005, which claims benefit of European patent application 04 019 137.1, filed Aug. 12, 2004.

Organometallic compounds—especially compounds of the $d^8$ metals—will in the near future find use as colouring components as functional materials in a number of applications of different types which can be ascribed to the electronics industry in the broadest sense. A development in this respect which has been evident in recent years is the use of organometallic iridium(III) complexes which exhibit phosphorescence instead of fluorescence (M. A. Baldo, S. Lamansky, P. E. Burrows, M. E. Thompson, S. R. Forrest, *Appl. Phys. Lett.* 1999, 75, 4-6). Efficient synthetic chemical access to the corresponding, high-purity organoiridium compounds is vital for successful industrial use. This is necessary both from economic points of view and also under the aspect of resource-conserving use of the said class of compounds.

As described in WO 02/060910 and WO 04/085449, homoleptic and heteroleptic iridium β-ketoketonates, in particular acetylacetonates (abbreviated below as acac), are particularly suitable as starting compounds for high-purity organoiridium compounds since high yields are obtained therewith. The homoleptic and heteroleptic ketoketonate complexes are furthermore suitable as catalysts or catalyst precursors for various organic reactions. They can also be employed as starting compound for, for example, ceramic colours, MOCVD (metal organic chemical vapour deposition) or heterogeneous catalysts. There is thus a great demand for these starting compounds.

The literature discloses various methods for the synthesis of homoleptic iridium β-ketoketonates:

Dwyer et al. (*J. Amer. Chem. Soc.* 1953, 75, 984) describe the synthesis starting from $K_2IrCl_6$. This process has the disadvantage of a very complex process procedure, which includes fuming with concentrated sulfuric acid, and the low yield of only 10%.

Davignon et al. (*J. Less Common Metals* 1970, 21, 345) describe three different processes, each of which only give yields between 5 and 15%.

Benett et al. (*Inorg. Chem.* 1976, 15, 2936) describe the synthesis of $Ir(acac)_3$ from $IrCl_3$ in pure Hacac using $NaHCO_3$ as base, where the product is separated by extraction with dichloromethane, which represents a health risk, and purified by column chromatography. A further disadvantage is the low yield of only 18%. The use of chromatographic methods on an industrial scale is also impracticable.

JP 07316176 discloses a process for the preparation of $Ir(acac)_3$ in which $IrCl_3$ is reacted with acetylacetone in water with addition of a base. The product is separated by extraction with benzene. In addition to the problematic use of carcinogenic benzene, the low yield of 20% is again disadvantageous here.

EP 1088812 discloses a process for the preparation of $Ir(acac)_3$ in which an iridium(IV) compound is reduced to iridium(III), reacted with acetylacetone at a pH of 6.5 to 7.5 at about 70° C., and the resultant precipitate is filtered off. Here too, the yields of about 22% are still unsatisfactory. A further disadvantage is the long reaction times in the order of 48 h.

All the methods described have a very low yield in common. There is thus no satisfactory and in particular resource-conserving process for the synthesis of $Ir(acac)_3$.

There have been virtually no reports in the literature of the synthesis of heteroleptic iridium β-ketoketonates with simple coligands not bonded to the metal via carbon. Only the synthesis of complexes which, in addition to two acac ligands, also contain one acac ligand bonded via carbon and a nitrogen-containing ligand, such as, for example, pyridine, is known (M. A. Bennett et al., *Inorg. Chem.* 1976, 15, 2936). However, this synthesis always gives a mixture with the homoleptic complex, which has to be separated off in a complex manner in a separate extraction step. However, it is precisely access to heteroleptic complexes as starting compound for further syntheses, as described above, that is also highly relevant.

The synthesis of the heteroleptic rhodium complex $Na[Rh(acac)_2Cl_2]$ (X. Y. Liu et al., *Organometallic* 2004, 23, 3584) can be carried out by reaction of rhodium chloride hydrate with acetylacetone and sodium hydrogencarbonate in methanol. The product is obtained in 58% yield after recrystallisation from methanol. However, an attempt to repeat the synthesis correspondingly with iridium chloride hydrate results in an undefined reaction mixture, meaning that the person skilled in the art is unable to draw any teaching from this publication regarding how corresponding heteroleptic iridium complexes could be accessible.

Surprisingly, it has now been found that homoleptic and heteroleptic iridium ketoketonate complexes are obtained simply, quickly and in very good yields if the reaction is carried out in at least two steps starting from an iridium(III) salt, with different solvents or solvent mixtures being used in each and the solvent of the reaction mixture being exchanged between the reaction steps.

The present invention accordingly describes a process for the preparation of iridium(III) complexes containing structural units of the formula (1)

$[L_nIrX_aY_a]$  Formula (1)

where:
X, Y are, identically or differently on each occurrence, a monodentate, monoanionic ligand which is bonded to the iridium via a heteroatom;
n is on each occurrence 2 or 3;
a is 0 if n=3 or is 1 if n=2;
L is on each occurrence, identically or differently, a ligand of the formula (2) which coordinates to Ir via both oxygen atoms

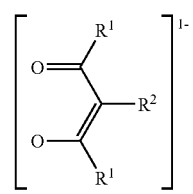

Formula (2)

where:
$R^1$, $R^2$ are, identically or differently on each occurrence, H, CN, a straight-chain, branched or cyclic alkyl or alkoxy group having 1 to 20 C atoms, in which one or more non-adjacent $CH_2$ groups may be replaced by —O—, —S—, —$NR^3$—, —$CONR^3$—, —CO—O—, —$CR^3$=$CR^3$— or —C≡C— and in which one or more H atoms may be replaced by F, or an aromatic or heteroaromatic ring system having 4 to 14 C atoms, which may be substituted by one or more non-aromatic radicals $R^1$; a plurality of substituents $R^1$ and/or $R^2$ here may together in turn form a further mono- or polycyclic, aliphatic or aromatic ring system;

$R^3$ is, identically or differently on each occurrence, H or an aliphatic or aromatic hydrocarbon radical having 1 to 20 C atoms, by reaction of an iridium(III) salt with compounds containing anions of the formula (2), characterised in that the starting materials are brought to reaction in a first solvent or solvent mixture, the solvent or solvent mixture is then partially or fully exchanged with substantial retention of the amount of substance of the salt-like components of the reaction mixture, and the reaction is completed in a further step in a further solvent or solvent mixture which is different from the first solvent or solvent mixture.

The structural units of the formula (1) are neutral complexes if n=3; for n=2, the structural units of the formula (1) are monoanions which also contain a counterion in the complex.

The complexes containing structural units of the formula (1) are preferably monocyclic complexes.

For the purposes of this invention, a solvent is taken to mean substances which are able to dissolve or suspend other substances by physical means without the solvent participating directly in the reaction, in particular without being incorporated permanently in the product as ligand into the coordination sphere of the iridium.

The solvent exchange according to the invention takes place here either continuously, or the intermediate is isolated and then reacted further in a second solvent or solvent mixture.

In accordance with the invention, the amount of substance of the salt-like components of the reaction mixture is maintained during solvent exchange. This means that the solvent exchange does not mean the removal by filtration of any precipitated fraction of the product already formed, with subsequent recrystallisation, as already described in the literature, since this only results in low yields. Salt-like components in the reaction mixture are, for example, all iridium compounds, base (for example hydrogencarbonate salts) and acetylacetonate anions, while, for example, excess non-deprotonated acetylacetone can be separated off at the same time during solvent exchange. Predominant retention of the amount of substance of the salt-like components means that a small amount of precipitated by-products can be filtered off and discarded or that some of the acetylacetonate, which is in equilibrium with acetylacetone, is not retained in the mixture due to evaporation. Preferably, however, filtration is not carried out between the two reaction steps.

The ligands of the formula (2) represent, depending on the meaning of the radical $R^1$, the corresponding anions of β-ketoketones, β-ketoesters or β-diesters.

A ligand X or Y which is bonded to the iridium via a heteroatom is taken to mean a ligand which is bonded to the iridium via an atom other than carbon; i.e. not organometallic ligands which form a direct iridium-carbon bond.

The homoleptic iridium(III) complexes prepared by the process according to the invention have a structure of the formula (3)

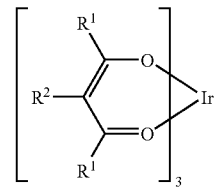

Formula (3)

where $R^1$, $R^2$ and $R^3$ have the above-mentioned meanings.

The heteroleptic iridium(III) complexes prepared by the process according to the invention preferably have a structure of the formula (4)

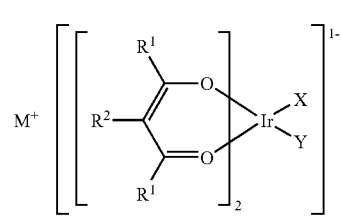

Formula (4)

where X, Y, $R^1$, $R^2$ and $R^3$ have the above-mentioned meanings, and $M^+$ represents a monovalent cation.

Particular preference is given to processes, characterised in that X=Y in formula (4). Compounds of the formula (4) where X=Y are particularly readily accessible, which gives rise to this preference.

The processes described frequently result in mixtures of isomeric heteroleptic iridium complexes of the formula (4). Accordingly, preference is given to processes according to the invention, characterised in that the heteroleptic iridium(III) complex of the formula (4) formed is a mixture of at least two isomers.

Particular preference is given to the processes described above, characterised in that the heteroleptic iridium(III) complex of the formula (4) formed is a mixture of the cis isomer of the formula (4a) and the trans isomer of the formula (4b) with respect to the X and Y anions

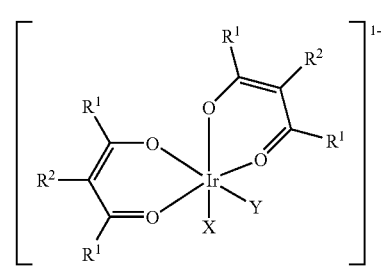

Formula (4a)

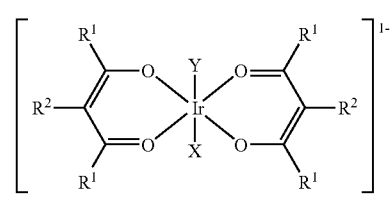

Formula (4b)

where $R^1$, $R^2$, $R^3$, X and Y have the above-mentioned meanings.

The coligands X and Y are preferably selected from the group of monodentate ligands consisting of $F^-$, $Cl^-$, $Br^-$, $I^-$, $OH^-$, $OR^-$, $CN^-$, $OCN^-$, $SCN^-$, $NO_2^-$, $NO_3^-$ and R—$COO^-$, where R stands for an organic radical having 1 to 20 C atoms, preferably for an alkyl chain. Particular preference is given to processes in which X and Y=$Cl^-$, $Br^-$ or $OH^-$, very particularly preferably $Cl^-$ or $Br^-$, in particular $Cl^-$.

The starting compound employed for the processes described above is preferably iridium(III) salts of the formula $IrX_3$ or $M_3IrX_6$, where M is equal to a proton, an alkali metal cation or an ammonium ion, and X has the above-mentioned meaning, or optionally a hydrate or hydrochloride hydrate of these salts.

Particular preference is given to the use of iridium(III) chloride in the form of the hydrate or hydrochloride hydrate of the formula $IrCl_3*yH_2O$ or $IrCl_3*xHCl*yH_2O$, where x=0 to 10 and y=0 to 100, preferably y=1 to 100, or of iridium(III) bromide in the form of the hydrate or hydrochloride hydrate of the formula $IrBr_3*yH_2O$ or $IrBr_3*xHCl*yH_2O$, where x and y have the above-mentioned meanings; very particular preference is given to the use of iridium(III)chloride in the form of the hydrate or hydrochloride hydrate of the above-mentioned formula.

It is also possible, if desired, firstly to employ an iridium (IV) compound, which is reduced in a first step to iridium(III), so that the actual process according to the invention again starts from iridium(III). Neither is it a hindrance to the process according to the invention for the corresponding iridium (III) compound also to contain fractions of iridium(IV).

The heteroleptic iridium(III) complexes prepared by the process according to the invention preferably have an alkali metal, alkaline earth metal, ammonium, tetraalkylammonium, tetraalkylphosphonium or tetraarylphosphonium cation as countercation M. Particular preference is given to processes according to the invention in which the iridium(III) complexes have an alkali metal cation, very particularly preferably sodium or potassium, as countercation.

Preference is furthermore given to processes in which $R^1$ and $R^2$, identically or differently on each occurrence, stand for H, a straight-chain, branched or cyclic alkyl or alkoxy group having 1 to 5 C atoms, in which, in addition, one or more H atoms may be replaced by fluorine, or an aryl or heteroaryl group having 4 to 6 C atoms, which may be substituted by one or more non-aromatic radicals $R^1$.

Particular preference is given to processes according to the invention, characterised in that $R^1$ is an alkyl group or fluoroalkyl group having 1 to 5 C atoms, very particularly preferably $CH_3$ or $CF_3$, in particular $CH_3$, and $R^2$=H. The ligand of the formula (2) thus very particularly preferably represents an acetylacetonate anion.

In accordance with the process according to the invention described above, the compound containing anions of the formula (2) is employed in the form of a salt of a monovalent or divalent inorganic or organic cation, preferably in the form of its lithium, sodium or potassium salt.

However, the ligand of the formula (2) can likewise be prepared in situ by deprotonation of the corresponding 1,3-diketone, 3-ketoester or 1,3-diester using a base. Alternatively, simple derivatives of the said anions, such as their Schiff bases, azomethines, oximes, hydrazones, acetals, ketals, hemiketals, aminals, etc., can also be employed, since these compounds can be hydrolysed in the first step by the solvent or solvent mixture in the presence of water to give the corresponding 1,3-diketones, 3-ketoesters or 1,3-diesters.

The water necessary for this purpose is either added directly as solvent or, where appropriate, originates from the water of hydration of the iridium salt.

The deprotonation of the 1,3-diketone, 3-ketoester or 1,3-diester with formation of the anions of the formula (2) is preferably carried out using hydrogencarbonate, carbonate or hydroxide, in particular the corresponding sodium or potassium salts, or using aqueous ammonia. The deprotonation is particularly preferably carried out using hydrogencarbonate, in particular sodium hydrogencarbonate or potassium hydrogencarbonate. It is furthermore also possible for the deprotonation not to be carried out by means of a separately added base, but instead by the counterion of the iridium compound if this is sufficiently basic, for example $Ir(OH)_3$.

The pH of the reaction solution is preferably between 3 and 8, particularly preferably between 4 and 7. It may also be sensible here repeatedly to reset the pH of the solution to a certain value during the reaction, in particular during the first reaction step, or to add the base in small portions.

The total stoichiometric ratio of iridium(III) salt to anions of the formula (2) is crucial for whether homoleptic complexes of the formula (3) or heteroleptic complexes of the formula (4) are formed, meaning that this ratio serves for control of the type of product desired.

A preferred embodiment of the process according to the invention is therefore characterised in that the total stoichiometric ratio of iridium(III) salt to anions of the formula (2) is 1:2 to 1:4, particularly preferably 1:2 to 1:3, very particularly preferably 1:2 to 1:2.5. This preference results from the observation that the total yield of product decreases if the ratio is below that mentioned, while the heteroleptic complex of the formula (4) is formed in very good yield if this ratio is observed. A further preferred embodiment of the process according to the invention is characterised in that the total stoichiometric ratio of iridium(III) salt to anions of the formula (2) is at least 1:4, preferably 1:4 to 1:100, particularly preferably 1:4 to 1:20, very particularly preferably 1:4 to 1:10. If this ratio is observed, the homoleptic complex of the formula (3) is obtained in very good yield.

In accordance with the invention, the molar ratio of iridium (III) salt to the corresponding 1,3-diketone, 3-ketoester or 1,3-diester from which the β-ketoketonate anion of the formula (2) is generated in situ by deprotonation is 1:2 to 1:100.

The concentration of iridium(III) salt in the reaction medium is preferably in the range from 0.1 to 1.0 mol/l.

The reaction is preferably carried out in a temperature range from 20° C. to 200° C., particularly preferably in a range from 50° C. to 150° C. It is very particularly preferred here for the reaction to be carried out in the corresponding solvent or solvent mixture under reflux. This relates to both reaction steps, before and after exchange of the solvent.

In accordance with the invention, the process is carried out in two (or if desired also more) steps, where the starting materials are brought to reaction in a first solvent or solvent mixture, all or some, preferably all, of the solvent is then exchanged with substantial retention of the amount of substance of the salt-like components, and the reaction is completed in a further reaction step in a further solvent or solvent mixture which is different from the first.

It is preferred here for the solvent (or solvent mixture) for the first reaction step to be more polar than the solvent (or solvent mixture) for the second reaction step. The dielectric constant of the solvent is considered here as a measure of the polarity, where the more polar solvent has the higher dielectric constant. Values for the dielectric constants of solvents are given, for example, in CRC *Handbook of Chemistry and Physics,* 62nd edition, 1981-1982, CRC Press, E52-E54.

The reaction media for the process according to the invention in all steps preferably comprise dipolar protic and/or dipolar aprotic solvents, and mixtures thereof.

The reaction media employed for the process according to the invention in all steps are preferably only dipolar protic or dipolar aprotic solvents, and mixtures thereof. Preferred dipolar protic solvents are water, alcohols, such as, for example, methanol, ethanol, n-propanol, i-propanol, n-butanol, i-butanol, t-butanol, ethylene glycol or propylene glycol, or also higher diols or polyalcohols, such as, for example, glycerol, or also polyether alcohols, such as polyethylene glycols. Preferred dipolar aprotic solvents are dimethyl sulfoxide, dimethylformamide, dimethylacetamide, acetone or N-methyl-2-pyrrolidinone. Particular preference is given to dipolar protic solvents in all reaction steps.

The starting materials and reaction products or intermediates are preferably dissolved predominantly or completely in the solvent or solvent mixture under reaction conditions.

The solvent used for the first reaction step before exchange of the solvent is preferably water or a mixture of water with a dipolar protic or dipolar aprotic solvent. The proportion of water here is preferably at least 50%. The solvent used for the first reaction step is particularly preferably water.

The solvent used for the second reaction step after exchange of the solvent is preferably one or more dipolar protic solvents, in particular alcohols, or mixtures of one or more dipolar protic solvents with water or one or more dipolar aprotic solvents. The solvent used for the second reaction step is particularly preferably an alcohol, very particularly preferably methanol or ethanol, in particular methanol.

The reaction time for the first reaction step is preferably between 1 h and 24 h, particularly preferably between 4 h and 12 h. The reaction time for the second reaction step is preferably between 1 h and 24 h, particularly preferably between 4 h and 12 h.

It is preferred for the intermediate or crude product to be isolated as solid between the two reaction steps. This can preferably be carried out by removal of the solvent, for example in vacuo and/or at elevated temperature. This furthermore has the advantage that an excess of non-deprotonated β-ketoketone, β-ketoester or β-diester can also be removed at the same time. In contrast to a filtration, removal of the solvent avoids separation-off of salt-like components, meaning that the entire reaction mixture is introduced into the second reaction step; a significantly higher yield is thus obtained.

It is also possible to exchange the solvents between the reaction steps in a continuous process. In this case, an intermediate or crude product is not isolated as solid. Continuous solvent exchange of this type is, for example, possible through continuous removal of a solvent by distillation (where appropriate as azeotrope) and correspondingly continuous addition of the second solvent. Furthermore, for continuous solvent exchange, it is possible to use, for example, a membrane which has higher permeability for the first solvent than for the second solvent. Particularly suitable here is pervaporation, in which a vapour mixture arising above the reaction solution as a consequence of different permeability of a suitable membrane is separated. By constant pumping-off of the vapour on the gas side of the membrane, a concentration gradient is produced, which maintains the diffusion.

In order to remove relatively small fractions of insoluble reaction by-products, it may be sensible to filter the cold or hot reaction solution. This can be carried out during or after the first reaction step and/or during or after the second reaction step. The filtration is preferably carried out after the second reaction step. Filtration and discarding of the residue is only sensible if the product does not precipitate out of the reaction mixture, since otherwise the yield is reduced. Preferably, no filtration is carried out between the first and second reaction steps The product can be isolated after the second reaction step by various methods, for example by crystallisation or by extraction. Isolation of the product by crystallisation is preferred here since the product is in this way accessible simply, in high purity and in good yield. At the same time, the use of relatively large amounts of possibly toxic, chlorinated and/or carcinogenic solvents is consequently avoided. For crystallisation, it may be helpful to concentrate and/or cool the reaction solution, preferably to <0° C., particularly preferably to <−10° C., after the second reaction step has been carried out (heating in the second solvent or solvent mixture), in order to increase the yield of the product. For further purification of the product, it can be washed, for example, with the solvent of the first and/or second reaction step or other solvents. Further purification methods familiar to the person skilled in the art, such as, for example, recrystallisation, are also possible, but are not absolutely necessary in the process according to the invention since the product is already formed in high purity.

A particularly preferred practical reaction procedure is, for example, the following, without wishing thereby to restrict the variety of possible variations:

An iridium(III) salt is brought to reaction with the desired amount of acetylacetone and the corresponding amount of base (depending on the desired product) in water under reflux. After evaporation to dryness in vacuo under elevated temperature, the residue is taken up in methanol, heated under reflux, filtered while hot, and the volume of the solution is concentrated. The product, complexes of the formula (3) or formula (4), crystallises out through cooling and can be isolated by filtration and washing with cold methanol and purified. Whether complexes of the formula (3) or formula (4) are formed here depends on the iridium:acetylacetonate ratio.

The process according to the invention is distinguished over the processes in accordance with the prior art by the following advantages:

1. By means of the process according to the invention, homoleptic iridium(III)ketoketonate compounds are readily accessible in very high yield of up to more than 60%, while only yields in the range from 5 to 22% are described in accordance with the prior art. This corresponds to an increase in the yield by a factor of approximately 3. This offers an enormous advantage for resource-conserving use of these rare metals.
2. By means of the process according to the invention, heteroleptic iridium(III)ketoketonate compounds are likewise accessible in very good yields. No syntheses are known to date for these heteroleptic compounds, but their accessibility as starting compounds for further syntheses is extremely important.
3. The process according to the invention does not require any solvents which represent a health risk, since the reaction can be carried out simply in water and alcohols and no extraction step with chlorine-containing solvents or benzene is necessary for isolation of the complexes.
4. The process according to the invention can also be used simply on an industrial scale since chromatographic methods are not required for the purification.

The complex mixtures synthesised by the process according to the invention are novel. This invention therefore furthermore relates to mixtures of complexes of the formulae (4a) and (4b) comprising 1 to 99% of complexes of the formula (4a) and 99 to 1% of complexes of the formula (4b). The mixture preferably comprises 20 to 80% of complexes of the formula (4a) and 80 to 20% of complexes of the formula (4b), particularly preferably 30 to 70% of complexes of the formula (4a) and 70 to 30% of complexes of the formula (4b), very particularly preferably 35 to 65% of complexes of the formula (4a) and 65 to 35% of complexes of the formula (4b).

The invention likewise relates to above-mentioned mixtures which also comprise further iridium complexes, for example complexes of the formula (3) or also other iridium complexes, in addition to complexes of the formula (4a) and complexes of the formula (4b).

The invention likewise relates to the above-mentioned complex mixtures obtainable by the process according to the invention described above.

The present invention is explained in greater detail by the following examples, but without wishing it to be restricted to the examples. It is thus possible for the person skilled in the art in the area of coordination chemistry to carry out the reactions according to the invention on further systems—as described above—without further inventive step.

EXAMPLES

The following syntheses were carried out without the use of a protective-gas atmosphere. The chemicals used (solvents, acetylacetone, sodium acetylacetonate, inorganic salts) were purchased from Aldrich (Taufkirchen, Germany). Iridium(III)chloride (hydrochloride) hydrate—calculated below in accordance with the idealised formula $IrCl_3 \cdot 3H_2O$— was purchased from Heraeus (Hanau, Germany).

Example 1

Sodium (bis(acetylacetonato)dichloro)iridate(III), (mixture of the cis and trans isomers) and tris(acetylacetonato)iridium(III)

About 200 ml of 1M aqueous sodium hydrogencarbonate solution and then 20.5 ml (200 mmol) of acetylacetone were added with vigorous stirring to a solution of 35.3 g (100 mmol) of $IrCl_3 \cdot 3H_2O$ in 200 ml of distilled water. The reaction mixture was heated at 100° C. for 10 h and evaporated to dryness in vacuo (1 mbar) at 80-90° C. The residue was taken up in 400 ml of methanol, heated under reflux for 8 h and filtered while hot (P4 frit). The filtrate was concentrated to a volume of 70 ml and stored at −20° C. for 24 h. The crystals formed were filtered off with suction, washed with a little cold methanol and dried. The yield of orange needle-like crystals was 23.1 g (48 mmol), corresponding to 47.7% of theory.

Analytical data of sodium (bis(acetylacetonato)dichloro) iridate(III):

$^1$H-NMR (DMSO-d6), mixture: δ [ppm]=5.35, 5.33, 1.82, 1.81, 1.71.

cis isomer: δ [ppm]=5.35 (s, 2H, CH), 1.82 (s, 6H, $CH_3$), 1.71 (s, 6H, $CH_3$).

trans isomer: δ [ppm]=5.33 (s, 2H, CH), 1.81 (s, 12H, $CH_3$).

cis:trans ratio=1.6:1.

$^{13}$C-{$^1$H}-NMR (DMSO-d6), mixture: δ [ppm]=183.28, 182.76, 181.68, 101.56, 101.25, 26.35, 26.15, 25.88.

cis isomer: δ [ppm]=183.28, 182.76 (CO), 101.25 (CH), 26.15, 25.88 ($CH_3$).

trans isomer: δ [ppm]=181.68 (CO), 101.56 (CH), 26.35 ($CH_3$).

MS (anions ESI): M$^-$=459.0, 460.0, 461.0, 461.9, 462.9, 464.0, 464.9.

EA: calc.=24.8% C, 2.9%; H, 14.6%; Cl, 39.7%; Ir. found=23.9% C, 2.8%; H, 15.0%; Cl, 39.2%; Ir.

Analytical data of tris(acetylacetonato)iridium(III) are described in Benett et al. (*Inorg. Chem.* 1976, 15, 2936).

Examples 2 to 8

Results of Variation of the Reaction Conditions

A number of experiments for the preparation of sodium (bis(acetylacetonato)dichloro)iridate(III), ($Na[Ir(acac)_2Cl_2]$) and tris(acetylacetonato)iridium(III) $Ir(acac)_3$ were carried out in accordance with the process indicated in Example 1.

The following table shows the molar ratios of the starting materials and the yield of product.

| Example | $IrCl_3 \cdot 3H_2O$ | Hacac | $NaHCO_3 \equiv acac^-$ | $Na[Ir(acac)_2Cl_2]$ [%] | $Ir(acac)_3$ [%] |
|---|---|---|---|---|---|
| 1 | 1 | 2 | 2 | 47.7 | 0 |
| 2 | 1 | 3 | 2 | 49.1 | 0 |
| 3 | 1 | 3 | 3 | 48.3 | 0 |
| 4 | 1 | 4 | 2 | 43.4 | 2 |
| 5 | 1 | 4 | 4 | 38.0 | 3.4 |
| 6 | 1 | 8 | 6 | 2.2 | 45.6 |
| 7 | 1 | 16 | 10 | 0 | 61.3 |
| 8 | 1 | 2* Naacac | — | 46.9 | 0 |

*For Example 8, sodium acetylacetonate was employed without further addition of a base.

Example 9

Sodium (bis(acetylacetonato)dichloro)iridate(III), (mixture of the cis and trans isomers) and tris(acetylacetonato)iridium(III)

A solution of 35.3 g (100 mmol) of $IrCl_3 \cdot 3H_2O$ in 200 ml of distilled water was adjusted to a pH=4.5+/−0.5 by addition of about 80 ml of 1M aqueous sodium hydrogencarbonate solution with vigorous stirring.

90.0 ml (875 mmol) of acetylacetone were subsequently added to the mixture, which was then heated under reflux for 30 min. After the mixture had been cooled to room temperature, the pH was reset to 4.5+/−0.5 by successive addition of about 20 to 40 ml of 1M aqueous sodium hydrogencarbonate solution. After the mixture had again been boiled under reflux for 12 h and cooled to room temperature, the pH was reset to 4.5+/−0.5 by successive addition of about 20 to 40 ml of 1M aqueous sodium hydrogencarbonate solution, and the mixture was heated under reflux for a further 6 h. The last-mentioned cycle of pH setting and heating under reflux for 6 h was repeated until a total of 300 ml of 1M aqueous sodium hydrogencarbonate solution had been consumed, corresponding to a total stoichiometric iridium:hydrogencarbonate ratio and thus a sodium acetylacetonate ratio of 1:3. The reaction mixture was subsequently evaporated to dryness in vacuo (1 mbar) at 80-90° C. The residue was taken up in 400 ml of methanol, heated under reflux for 8 h and filtered while hot (P4). The filtrate was concentrated to a volume of 70 ml and stored at −20° C. for 24 h. The crystals formed were filtered off with suction, washed with a little cold methanol and dried. The yield of orange needle-like crystals was 23.6 g (49 mmol), corresponding to 48.7% of theory.

Analytical data see Example 1.

Examples 10 to 16

Results of Variation of the Reaction Conditions

A number of experiments for the preparation of sodium (bis(acetylacetonato)dichloro)iridate(III), ($Na[Ir(acac)_2Cl_2]$)

and tris(acetylacetonato)iridium(III) Ir(acac)$_3$ were carried out in accordance with the procedure indicated in Example 9.

The following table shows the molar ratios of the starting materials and the yield of product.

| Example | IrCl$_3$·3H$_2$O | Hacac | NaHCO$_3$=acac$^-$ | Na[Ir(acac)$_2$Cl$_2$] [%] | Ir(acac)$_3$ [%] |
|---|---|---|---|---|---|
| 9 | 1 | 8.75 | 3 | 48.7 | 0 |
| 10 | 1 | 8.75 | 2 | 41.0 | 0 |
| 11 | 1 | 8.75 | 3.5 | 47.9 | 0 |
| 12 | 1 | 8.75 | 4 | 47.1 | 2.0 |
| 13 | 1 | 8.75 | 4.5 | 31.8 | 24.5 |
| 14 | 1 | 8.75 | 5 | 21.0 | 33.1 |
| 15 | 1 | 8.75 | 6 | 1.7 | 61.4 |
| 16 | 1 | 16 | 3 | 49.0 | 0 |

Example 17

Tris(acetylacetonato)iridium(III) (Comparative Example)

About 600 ml of 1M aqueous sodium hydrogencarbonate solution and then 82.3 ml (800 mmol) of acetylacetone were added with vigorous stirring to a solution of 35.3 g (100 mmol) of IrCl$_3$.3H$_2$O in 200 ml of distilled water. The reaction mixture was heated at 100° C. for 10 h and allowed to cool. The yellow precipitate was filtered off with suction and washed three times with each of water (50 ml) and methanol (20 ml). The yield was 8.3 g (17 mmol), corresponding to 17.0% of theory. It was not possible to detect a defined product in the mother liquor.

Example 18

Tris(acetylacetonato)iridium(III) (Comparative Example)

50.4 g (600 mmol) of sodium hydrogencarbonate and then 82.3 ml (800 mmol) of acetylacetone were added to a solution of 35.3 g (100 mmol) of IrCl$_3$.3H$_2$O in 400 ml of methanol. The reaction mixture was heated under reflux for 10 h and allowed to cool. No tris(acetylacetonato)iridium(III) precipitated out. No tris(acetylacetonato)iridium(III) crystallised out even after concentration to about 150 ml, and no defined product was detectable in the reaction solution.

Example 19

Tris(acetylacetonato)iridium(III) (Comparative Example)

The reaction was carried out as in Example 17 with the difference that the reaction was carried out in 100 ml of distilled water and 100 ml of methanol. A yellow pre-cipitate was formed, which was filtered off with suction and washed with cold methanol. The yield was 5.9 g (12 mmol), corresponding to 12% of theory. It was not possible to detect a defined product in the mother liquor.

As is thus evident from Examples 1 to 16 according to the invention, homoleptic and heteroleptic iridium ketoketonate compounds can be synthesised in very good yield by the process according to the invention. If, by contrast, the reaction is carried out only in water in accordance with the prior art, the yield of iridium complex is significantly lower. If the reaction is carried out only in methanol, no defined product at all can be isolated.

The invention claimed is:

1. A process for the preparation of iridium(III) complexes containing structural units of formula (1)

$$[L_n IrX_a Y_a]^x \qquad \text{Formula (1)}$$

wherein

X and Y are, identically or differently on each occurrence, a monodentate, monoanionic ligand which is bonded to the iridium via a heteroatom;

n is on each occurrence 2 or 3;

a is 0 if n is 3 and is 1 if n is 2;

x is −1 when n is 2 and a is 1 and x is 0 when n is 3 and a is 0;

L is on each occurrence, identically or differently, a ligand of formula (2) which coordinates to Ir via both oxygen atoms

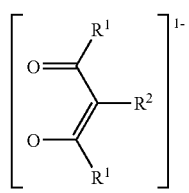

Formula (2)

wherein

R$^1$ and R$^2$ are, identically or differently on each occurrence, H, CN, a straight-chain, branched or cyclic alkyl group having up to 20 C atoms, or a straight-chain, branched or cyclic alkoxy group having up to 20 C atoms, wherein one or more non-adjacent CH$_2$ groups of said alkyl or alkoxy groups are optionally replaced by —O—, —S—, —NR$^3$—, —CONR$^3$—, —CO—O—, —CR$^3$=CR$^3$— or —C≡C— and wherein one or more H atoms may be replaced by F, or an aromatic or heteroaromatic ring system having 4 to 14 C atoms, wherein said aromatic or heteroaromatic ring systems may be substituted by one or more non-aromatic radicals R$^1$; and wherein a plurality of substituents R$^1$ and/or R$^2$ together optionally define a monocyclic or polycyclic aliphatic ring system or a monocyclic or polycyclic aromatic ring system; and R$^3$ is, identically or differently on each occurrence, H or an aliphatic or aromatic hydrocarbon radical having up to 20 C atoms, comprising the steps of (1) reacting an iridium(III) salt starting compound with compounds containing anions of the formula (2) in a first solvent or solvent mixture, (2) partially or fully exchanging the first solvent or solvent mixture with a second solvent or solvent mixture, which is different from the first solvent or solvent mixture, while substantially retaining the amount of the salt-like components of the reaction mixture, and (3) completing the reaction in said second solvent or solvent mixture.

2. The process according to claim 1, wherein homoleptic iridium (III) complexes of formula (3)

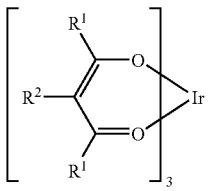

Formula (3)

are obtained, wherein $R^1$ and $R^2$ are, identically or differently on each occurrence, H, CN, a straight-chain, branched or cyclic alkyl group having up to 20 C atoms, or a straight-chain, branched or cyclic alkoxy group having up to 20 C atoms, wherein one or more non-adjacent $CH_2$ groups of said alkyl or alkoxy groups are optionally replaced by —O—, —S—, —$NR^3$—, —$CONR^3$—, —CO—O—, —$CR^3$=$CR^3$— or —C≡C— and wherein one or more H atoms may be replaced by F, or an aromatic or heteroaromatic ring system having 4 to 14 C atoms, wherein said aromatic or heteroaromatic ring systems may be substituted by one or more non-aromatic radicals $R^1$; and wherein a plurality of substituents $R^1$ and/or $R^2$ together optionally define a monocyclic or polycyclic aliphatic ring system or a monocyclic or polycyclic aromatic ring system; and $R^3$ is, identically or differently on each occurrence, H or an aliphatic or aromatic hydrocarbon radical having up to 20 C atoms.

3. The process according to claim 1, wherein heteroleptic iridium(III) complexes of formula (4)

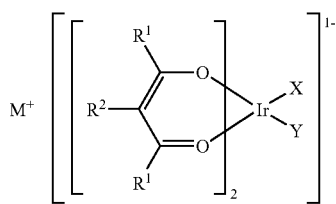

Formula (4)

are obtained, wherein

X and Y are, identically or differently on each occurrence, a monodentate, monoanionic ligand which is bonded to the iridium via a heteroatom;

$R^1$ and $R^2$ are, identically or differently on each occurrence, H, CN, a straight-chain, branched or cyclic alkyl group having up to 20 C atoms, or a straight-chain, branched or cyclic alkoxy group having up to 20 C atoms, wherein one or more non-adjacent $CH_2$ groups of said alkyl or alkoxy groups are optionally replaced by —O—, —S—, —$NR^3$—, —$CONR^3$—, —CO—O—, —$CR^3$=$CR^3$— or —C≡C— and wherein one or more H atoms may be replaced by F, or an aromatic or heteroaromatic ring system having 4 to 14 C atoms, wherein said aromatic or heteroaromatic ring systems may be substituted by one or more non-aromatic radicals $R^1$; and wherein a plurality of substituents $R^1$ and/or $R^2$ together optionally define a monocyclic or polycyclic aliphatic ring system or a monocyclic or polycyclic aromatic ring system;

$R^3$ is, identically or differently on each occurrence, H or an aliphatic or aromatic hydrocarbon radical having up to 20 C atoms; and $M^+$ is a monovalent cation.

4. The process according to claim 1, wherein X and Y are, identically, a monodentate, monoanionic ligand which is bonded to the iridium via a heteroatom.

5. The process according to claim 1, wherein the heteroleptic iridium(III) complex formed is a mixture of the cis isomer (formula 4a) and the trans isomer (formula 4b) with respect to the X and Y ligands

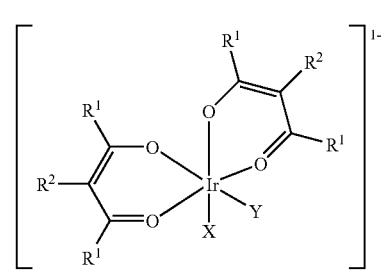

Formula (4a)

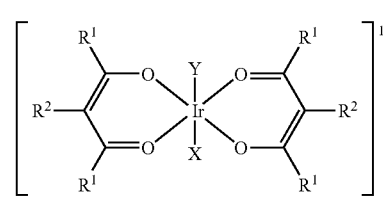

Formula (4b)

and wherein

X and Y are, identically or differently on each occurrence, a mono dentate, monoanionic ligand which is bonded to the iridium via a hetero atom;

$R^1$ and $R^2$ are, identically or differently on each occurrence, H, CN, a straight-chain, branched or cyclic alkyl group having up to 20 C atoms, or a straight-chain, branched or cyclic alkoxy group having up to 20 C atoms, wherein one or more non-adjacent $CH_2$ groups of said alkyl or alkoxy groups are optionally replaced by —O—, —S—, —$NR^3$, —$CONR^3$—, —CO—O—, —$CR^3$=$CR^3$— or —C≡C— and wherein one or more H atoms may be replaced by F, or an aromatic or heteroaromatic ring system having 4 to 14 C atoms, wherein said aromatic or heteroaromatic ring systems may be substituted by one or more non-aromatic radicals $R^1$ and wherein a plurality of substituents $R^1$ and/or $R^2$ together optionally define a monocyclic or polycyclic aliphatic ring system or a monocyclic or polycyclic aromatic ring system; and $R^3$ is, identically or differently on each occurrence, H or an aliphatic or aromatic hydrocarbon radical having up to 20 C atoms.

6. The process according to claim 1, wherein X and Y are selected from the group consisting of F⁻, Cl⁻, Br⁻, I⁻, OH⁻, OR⁻, CN⁻, OCN⁻, SCN⁻, $NO_2^-$, $NO_3^-$ and R—COO⁻, wherein R is an organic radical having up to 20 C atoms.

7. The process according to claim 6, wherein X and Y are, identically or differently on each occurrence, Cl⁻, Br⁻, or OH⁻.

8. The process according to claim 1, wherein the starting compound employed is an iridium (III) salt or salts having formula $IrX_3$ or $M_3IrX_6$, or, optionally, a hydrate or hydrochloride hydrate thereof, wherein M is a proton, an alkali metal cation, or an ammonium ion, and wherein X is a monodentate, monoanionic ligand which is bonded to the iridium via a heteroatom.

9. The process according to claim 8, wherein said starting compound is iridium (III) chloride in the form of the hydrate or hydrochloride hydrate having a formula $IrCl_3*yH_2O$ or $IrCl_3*xHCl*yH_2O$, wherein x is 0 to 10 and y is 0 to 100.

10. The process according to claim 3, wherein the heteroleptic iridium (III) complexes of formula (4) have an alkali metal, alkaline earth metal, ammonium, tetraalkylammonium, tetraalkylphosphonium or tetraarylphosphonium cation as a counter-cation.

11. The process according to claim 10, wherein said heteroleptic iridium (III) complexes have an alkali metal cation as counter-cation.

12. The process according to claim 1, wherein $R^1$ and $R^2$ are, identically or differently on each occurrence, H, a straight-chain, branched or cyclic alkyl group having 1 to 5 C atoms or a straight-chain, branched or cyclic alkoxy group having 1 to 5 C atoms, and wherein one or more H atoms are optionally replaced by F, or an aryl or heteroaryl group having 4 to 6 C atoms, which are optionally substituted by one or more non-aromatic radicals $R^1$.

13. The process according to claim 12, wherein $R^1$ is $CH_3$ and $R^2$ is H.

14. The process according to claim 1, wherein the compounds containing anions of formula (2) are employed in the form of a salt of a monovalent or divalent inorganic or organic cation or are prepared in situ by deprotonation of the corresponding 1,3-diketone, 3-ketoester, or 1,3-diester using a base.

15. The process according to claim 14, wherein the deprotonation of the 1,3-diketone, 3-ketoester, or 1,3-diester is carried out using hydrogencarbonate, carbonate, hydroxide or aqueous ammonia.

16. The process according to claim 3, wherein the total stoichiometric ratio of iridium (III) salt to anions of the formula (2) is 1:2 to 1:4.

17. The process according to claim 2, wherein the total stoichiometric ratio of iridium (III) salt to anions of the formula (2) is at least 1:4.

18. The process according to claim 1, wherein the reaction is carried out in a temperature range from 20° C. to 200° C.

19. The process according to claim 18, wherein the reaction is carried out under reflux.

20. The process according to claim 1, wherein the first solvent or solvent mixture is more polar than the second solvent or solvent mixture.

21. The process according to claim 1, wherein the first and second solvent or solvent mixtures are dipolar protic solvents, dipolar aprotic solvents, or mixtures thereof.

22. The process according to claim 21, wherein the first and second solvent or solvent mixtures selected from the group consisting of water, alcohols, glycols, higher diols, polyalcohols, polyether alcohols, dimethyl sulfoxide, dimethylformamide, dimethylacetamide, acetone, and N-methyl-2-pyrrolidinone.

23. The process according to claim 1, wherein the first solvent is water.

24. The process according to claim 1, wherein the second solvent is an alcohol.

25. The process according to claim 24, wherein the second solvent is methanol.

26. The process according to claim 1, further comprising the additional step of isolating an intermediate or crude product as a solid after step (1).

27. The process according to claim 2, further comprising the additional step of isolating the homoleptic iridium(III) complexes of formula (3) by crystallisation, by concentration of the second solvent or solvent mixture, by cooling, or by any combination thereof.

28. The process according to claim 3, further comprising the additional step of isolating the heteroleptic iridium(III) complexes of formula (4) by crystallisation, by concentration of the second solvent or solvent mixture, by cooling, or by any combination thereof.

29. Mixtures of complexes of formulae (4a) and (4b)

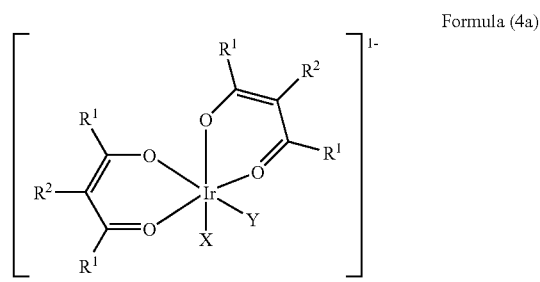

Formula (4a)

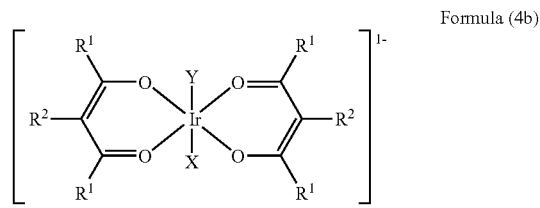

Formula (4b)

wherein

X and Y are, identically or differently on each occurrence, a monodentate, monoanionic ligand which is bonded to the iridium via a heteroatom;

$R^1$ and $R^2$ are, identically or differently on each occurrence, H, CN, a straight-chain, branched or cyclic alkyl group having up to 20 C atoms, or a straight-chain, branched or cyclic alkoxy group having up to 20 C atoms, wherein one or more non-adjacent $CH_2$ groups of said alkyl or alkoxy groups are optionally replaced by —O—, —S—, —$NR^3$—, —$CONR^3$—, —CO—O—, —$CR^3$=$CR^3$— or —C≡C— and wherein one or more H atoms may be replaced by F, or an aromatic or heteroaromatic ring system having 4 to 14 C atoms, wherein said aromatic or heteroaromatic ring systems may be substituted by one or more non-aromatic radicals $R^1$; and wherein a plurality of substituents $R^1$ and/or $R^2$ together optionally define a monocyclic or polycyclic aliphatic ring system or a monocyclic or polycyclic aromatic ring system; and $R^3$ is, identically or differently on each occurrence, H or an aliphatic or aromatic hydrocarbon radical having up to 20 C atoms:

wherein said mixtures comprise 1 to 99% of complexes of formula (4a) and 99 to 1% of complexes of formula (4b).

30. The mixtures of claim 29, wherein said mixtures further comprise iridium complexes that are not of formulae (4a) or (4b).

31. Mixtures of complexes of formulae (4a) and (4b)

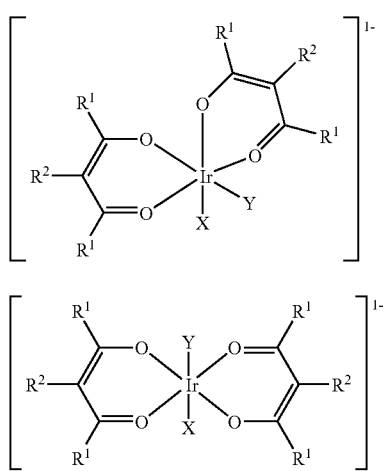

wherein

X and Y are, identically or differently on each occurrence, a monodentate, monoanionic ligand which is bonded to the iridium via a heteroatom;

$R^1$ and $R^2$ are, identically or differently on each occurrence, H, CN, a straight-chain, branched or cyclic alkyl group having up to 20 C atoms, or a straight-chain, branched or cyclic alkoxy group having up to 20 C atoms, wherein one or more non-adjacent $CH_2$ groups of said alkyl or alkoxy groups are optionally replaced by —O—, —S—, —$NR^3$—, —$CONR^3$—, —CO—O—, —$CR^3$=$CR^3$— or —C≡C— and wherein one or more H atoms may be replaced by F, or an aromatic or heteroaromatic ring system having 4 to 14 C atoms, wherein said aromatic or heteroaromatic ring systems may be substituted by one or more non-aromatic radicals $R^1$; and wherein a plurality of substituents $R^1$ and/or $R^2$ together optionally define a monocyclic or polycyclic aliphatic ring system or a monocyclic or polycyclic aromatic ring system; and $R^3$ is, identically or differently on each occurrence, H or an aliphatic or aromatic hydrocarbon radical having up to 20 C atoms;

wherein said complexes of formulae (4a) and (4b) are prepared according to the process of claim 1; and wherein said mixtures comprise 1 to 99% of complexes of formula (4a) and 99 to 1% of complexes of formula (4b).

32. The mixtures of claim 31, wherein said mixtures further comprise iridium complexes that are not of formulae (4a) or (4b).

* * * * *